(12) United States Patent
Tunnell et al.

(10) Patent No.: US 11,024,142 B2
(45) Date of Patent: Jun. 1, 2021

(54) EVENT DETECTOR FOR ISSUING A NOTIFICATION RESPONSIVE TO OCCURRENCE OF AN EVENT

(71) Applicant: NXT-ID, INC., Shelton, CT (US)

(72) Inventors: David Tunnell, Palm Bay, FL (US); Jonathan Larson, Novato, FL (US); Kevin O'Connor, Plymouth, MN (US)

(73) Assignee: NXT-ID, INC., Shelton, CT (US)

( * ) Notice: Subject to any disclaimer, the term of this patent is extended or adjusted under 35 U.S.C. 154(b) by 73 days.

(21) Appl. No.: 16/048,181

(22) Filed: Jul. 27, 2018

(65) Prior Publication Data

US 2019/0088101 A1   Mar. 21, 2019

Related U.S. Application Data

(60) Provisional application No. 62/537,904, filed on Jul. 27, 2017, provisional application No. 62/537,633, filed on Jul. 27, 2017.

(51) Int. Cl.
| | |
|---|---|
| *G08B 21/22* | (2006.01) |
| *G16H 20/30* | (2018.01) |
| *G16H 40/67* | (2018.01) |
| *G16H 50/70* | (2018.01) |
| *G16H 50/20* | (2018.01) |
| *G16H 20/10* | (2018.01) |
| *G08B 21/02* | (2006.01) |
| *G08B 25/10* | (2006.01) |
| *G08B 21/04* | (2006.01) |
| *G08B 25/01* | (2006.01) |
| *G08B 27/00* | (2006.01) |
| *G08B 25/00* | (2006.01) |

(52) U.S. Cl.
CPC ........... *G08B 21/043* (2013.01); *G08B 21/02* (2013.01); *G08B 21/0216* (2013.01); *G08B 21/0272* (2013.01); *G08B 21/0415* (2013.01); *G08B 21/0446* (2013.01); *G08B 21/0453* (2013.01); *G08B 25/016* (2013.01); *G16H 20/10* (2018.01); *G16H 20/30* (2018.01); *G16H 40/67* (2018.01); *G16H 50/20* (2018.01); *G16H 50/70* (2018.01); *G08B 25/002* (2013.01); *G08B 25/10* (2013.01); *G08B 27/005* (2013.01)

(58) Field of Classification Search
CPC ..................................................... G16H 50/20
See application file for complete search history.

(56) References Cited

U.S. PATENT DOCUMENTS

| | | |
|---|---|---|
| 6,151,385 A | 11/2000 | Reich |
| 6,160,478 A | 12/2000 | Jacobsen et al. |
| 6,333,694 B2 | 12/2001 | Pierce et al. |

(Continued)

*Primary Examiner* — Joseph H Feild
*Assistant Examiner* — Pameshanand Mahase
(74) *Attorney, Agent, or Firm* — Wolter Van Dyke Davis, PLLC; John L. DeAngelis

(57) ABSTRACT

A system for determining the occurrence of an event and for issuing notifications responsive the occurrence of the event. The system has a first component for storing reference parameters for use in determining occurrence of the event and a sensor for determining real-time parameters that may be indicative of the occurrence of the event. An analysis component analyzes the real-time parameters relative to the reference parameters. If the event is detected a communications component issues a notification to those effected by the event.

30 Claims, 5 Drawing Sheets

(56) References Cited

U.S. PATENT DOCUMENTS

| | | |
|---|---|---|
| 6,504,909 B1 | 1/2003 | Cook |
| 6,775,356 B2 | 8/2004 | Salvucci |
| 7,312,709 B2 | 12/2007 | Kingston |
| 7,893,844 B2 | 2/2011 | Gottlieb |
| 7,916,066 B1 | 3/2011 | Osterweil |
| 8,005,456 B2 | 8/2011 | Buehler |
| 8,115,641 B1 | 2/2012 | Dempsey |
| 8,116,724 B2 | 2/2012 | Peabody |
| 8,121,588 B2 | 2/2012 | Gottlieb |
| 8,206,325 B1 | 6/2012 | Najafi |
| 8,265,687 B2 | 9/2012 | D'Evelyn |
| 8,275,346 B2 | 9/2012 | Gottlieb |
| 8,369,821 B2 | 2/2013 | Gottlieb |
| 8,370,106 B2 | 2/2013 | Shkolnikov |
| 8,441,356 B1 | 5/2013 | Tedesco et al. |
| 8,515,022 B2 | 8/2013 | Wooding |
| 8,653,965 B1 | 2/2014 | Otto |
| 8,752,375 B2 | 6/2014 | Berchowitz |
| 8,779,919 B1 | 7/2014 | Darling |
| D710,230 S | 8/2014 | Burke |
| 8,811,964 B2 | 8/2014 | Fish |
| 8,812,258 B2 | 8/2014 | Nadkarni |
| 8,843,101 B2 | 9/2014 | Fish |
| 8,866,606 B1 | 10/2014 | Will |
| 8,868,616 B1 | 10/2014 | Otto |
| 8,909,497 B1 | 12/2014 | Shkolnikov |
| 8,912,899 B2 | 12/2014 | Otto |
| 8,938,210 B1 | 1/2015 | Otto |
| 8,972,197 B2 | 3/2015 | Jangle |
| 9,005,141 B1 | 4/2015 | Najafi |
| 9,143,600 B2 | 9/2015 | Fish |
| 9,179,564 B2 | 11/2015 | Sechrist |
| 9,179,864 B2 | 11/2015 | Otto |
| 9,192,899 B2 | 11/2015 | Sumiya |
| 9,288,329 B2 | 3/2016 | Newton |
| 9,295,412 B2 | 3/2016 | Otto |
| 9,311,789 B1 | 4/2016 | Gwin |
| 9,396,645 B2 | 7/2016 | Will |
| 9,451,795 B2 | 9/2016 | Krueger |
| 9,462,444 B1 | 10/2016 | Fish |
| 9,470,704 B2 | 10/2016 | Nadkarni |
| 9,497,609 B2 | 11/2016 | Otto |
| 9,526,420 B2 | 12/2016 | Fish |
| 9,547,977 B2 | 1/2017 | Will |
| 9,641,620 B2 | 5/2017 | Sweeney |
| 9,648,478 B2 | 5/2017 | Fish |
| 9,734,690 B2 | 8/2017 | Haflinger |
| 9,772,671 B1 | 9/2017 | Lee |
| 9,805,577 B2 | 10/2017 | Haflinger |
| 9,875,450 B1 | 1/2018 | Hendrick, III |
| 9,892,612 B2 | 2/2018 | Smits |
| 9,900,737 B2 | 2/2018 | Larson |
| 9,901,290 B2 | 2/2018 | Najafi |
| 9,906,930 B2 | 2/2018 | Blando |
| 2002/0057764 A1 | 5/2002 | Salvucci |
| 2004/0105529 A1 | 6/2004 | Salvucci |
| 2012/0242501 A1* | 9/2012 | Tran ............... A61B 5/7465 340/870.02 |
| 2013/0211291 A1* | 8/2013 | Tran ............... G16H 50/20 600/595 |
| 2015/0221202 A1* | 8/2015 | Russell ............... A61B 5/1117 340/573.7 |
| 2015/0374896 A1* | 12/2015 | Du ............... A61M 1/3656 604/111 |
| 2016/0142894 A1 | 5/2016 | Papakonstantinou et al. |
| 2017/0056724 A1 | 3/2017 | Baker |
| 2017/0095674 A1* | 4/2017 | Hresko ............... A61N 1/3937 |
| 2017/0116845 A1* | 4/2017 | See ............... G08B 25/016 |
| 2018/0068614 A1 | 3/2018 | Breedvelt-Schouten |
| 2018/0189449 A1 | 7/2018 | Karumba et al. |

* cited by examiner

EVENT DETECTOR FOR ISSUING A NOTIFICATION RESPONSIVE TO OCCURRENCE OF AN EVENT

CROSS REFERENCE TO RELATED APPLICATIONS

The present application claims priority to the provisional patent application assigned application No. 62/537,633, filed on Jul. 27, 2017 and to the provisional patent application assigned application No. 62/537,904, filed on Jul. 27, 2017, both of which are incorporated herein in their entirety.

FIELD OF INVENTION

The present invention is directed to a method and system for detecting an event and in response thereto utilizing an alert-based social network (also referred to herein as a private health (or event) management social network.

BACKGROUND OF THE INVENTION

Remote personal monitoring typically consists of centralized call centers that monitor the status of one or more persons. While personal monitoring spans a number of industries, it can be generally described to fall into two primary categories; Health Management or Safety. Typically, an alert generated by a central notification device in response to a detected event sends a signal to a call or crisis center for assistance. Mechanisms that facilitate alerts typically span a person manually pressing a panic button to sensing changes in a person's physiology. Alerts are also initiated responsive to detection of a fall or detection of non-responsiveness.

Of the 35 million Americans over 65, about 1 in 3 will fall in a given year, and 50% of those people who fall require assistance from someone to get back up. Seniors are hospitalized for fall-related injuries 5 times more often than they are for injuries from all other causes. Falls are the leading cause of accidental death for seniors. Research shows that with prompt attention and assistance, the survival rate for the individual is higher. The ability to summon and receive assistance easily and quickly encourages seniors to live independently. But the longer a person spends in a helpless situation, unable to summon and receive help, the greater the likelihood that he/she will require treatment at a supportive care facility.

Fall detection is also important for many other applications such as the "lone worker" where no one is present to detect when an individual has fallen or become incapacitated. For elderly people who live alone, suffering an incapacitated condition and unable to summon help is a common worry, which usually marks the end of his/her independent living arrangement. Statistics have shown that after a fall or other emergency, 90% of people who receive assistance within one hour will continue independent living after receiving treatment, but for those receiving help after 12 hours, only 10% continue to live independently.

Fall detectors currently exist and typically fall into three categories: shock detection, non-movement and orientation sensing. In the first shock detection category, the unit detects a shock triggered by the fall event. The second non-movement category is typically detected using a motion sensor, such an accelerometer. The third category typically employs a tilt switch (e.g., a mercury switch or equivalent) embedded in an object that must be worn on the person. When the person and the object falls, for example, a horizontal orientation of the wearer and the object triggers the tilt switch.

However, a shock can be detected by a shock sensor worn on a person when the person only bumps into a counter while walking around the home. Also, when one has a serious event (e.g., a sudden cardiac arrest), the person may not fall violently to the ground. Instead, the person may just slowly collapse to the ground thereby not triggering the shock sensor. The tilt sensor likewise has drawbacks including that it must be disabled each time the person wants to lie down (e.g., to take a nap or go to bed for the evening).

Other health related events such as but not limited to blood sugar, blood pressure, pulse variations (also referred to a medical related parameters) and the like may contribute to the overall health management of seniors. Likewise, simple "panic buttons" are frequently used to alert another party of potential threat to the safety of the wearer.

BRIEF DESCRIPTION OF THE DRAWINGS

The following description, given with respect to the attached drawings, may be better understood with reference to the non-limiting examples of the drawings, wherein.

DETAILED DISCUSSION OF THE INVENTION

Introduction

Figure 1:
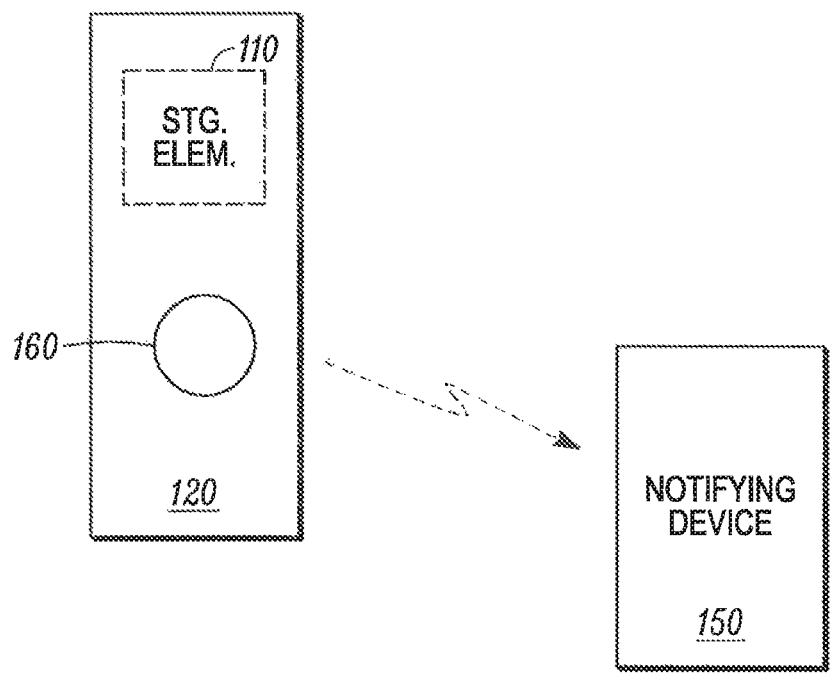
FIG. 1 is a block diagram of a fall detection system of one embodiment of the invention.

Today there is a plethora of data available that can be collected and analyzed on behalf of a person, individual, subject, animal, device, computer, wearer, robot or any other object able to be characterized (called an "entity" herein) for determining various actions an entity may wish to perform, such as but not limited to comparing or modifying fitness routines, alerts for possible health related matters or other events, emergency responses of an individual or entity, data transfers, conducting a transaction or executing a task, as non-limiting examples.

Various systems are described herein for accomplishing various actions, such as detecting or predicting a fall, medical emergency, safety or another security event, including an event that requires assistance from another entity. Such systems are beneficial to a variety of industries, markets and applications including hospitality, housekeeping, health and medical, education (such as active shooter detection), empty warehouse or other area, fire and entry, detention and/or correction facilities, suicide prevention, enterprise, retail, real estate, and many others where entities live and work alone or requiring monitoring.

SUMMARY

Such event detection systems or devices (also referred to herein as sensing devices) may comprise one or more devices that perform various functions of sensing, triggering, alerting, notifying, and responding. Devices may take many forms such as but not limited to wearables, mobile, portable, or other form factors that can be hung on a wall and/or embedded into other devices such as but not limited to door knobs, picture frames and the like. Some devices may be comprised of one or more of the following: MCU (Micro-controller unit), various sensors, communication methods, RF, antennas, motion detectors, microphones, speakers, indicators such as LEDs, speakers, displays and the like. Devices that collect data and/or contain one or more buttons and or sensors are called "event detection devices" or "sensing devices" herein.

Devices and/or services that may send alerts to one or more devices or services are called "alerting devices" herein. Devices and/or services that notify other devices are called "notification devices" herein. Responding devices that receive notifications and/or take some action are called "responding devices" herein. In some embodiments, the one device may provide the functionality of combinations or all features of these devices as described above.

As described herein, the nouns, vitals, metrics, and measurements are generally used interchangeably to refer to a condition or parameter that may be influenced by the occurrence of an event, in particular to a health-related event.

Summary of Sensors

To accomplish their objectives, devices may sense various parameters related to biometrics, knowledge metrics, electronic metrics, physical activities, behavior metrics (e.g. behaviors), and/or psychological indicators of a subject. These parameters can be sensed, analyzed and/or stored locally and/or remotely on another server, cloud and/or portal. The collected data may be analyzed at any time to invoke an indicated response on behalf of the entity, and/or retrieved and viewed to manage of the care and/or alerts of an entity.

Parameters in this context are equivalent to metrics, measurements, vitals, statistics and other data that can be collected regarding an entity that could be utilized to determine status (e.g. health, wealth, states such as but not limited to emotional states, safety and the like).

Physiological (or biometric) parameters may include: heart rate, blood pressure, blood type, oxygen saturation, heart rhythms, body temperature, breathing patterns, breathing index, fatigue, stress, dizziness, fall prediction, fall detection, motion sickness, pain level, brain waves, brain wave patterns, sleep patterns, blood chemistry, sweat chemistry, respiration rate, shock indicators, urinalysis, medication intake, missed medications, overdose, caloric intake, blood sugar level, water and/or hydration level, posture, weight, height, gait, eye color, IRIS, hand, fingerprint, face, voice, audio print, iris print, voice pitch, dimensions of a body part, facial dimensions, facial response and/or expression, galvanic skin response, odor and/or scent, pheromone, electrocardiogram, electroencephalograph, blood alcohol level, drug presence or level, and the like.

Knowledge metrics or knowledge parameters may include, for non-limiting example, passwords, phrases, keys, numbers, PINs (Personal Identification Numbers), and/or any individual or combination of parameters that are unique that only the entity would know.

Electronic metrics refer to emissions from an electronic device, which may be distinctive relative to an electronic emission from another electronic device. These electronic metrics are signal characteristics that are unique to an electronic device that can be collected and analyzed to identify the specific electronic device. Electronic metrics may also be used to analyze the health or status of some electronics by detecting changes in the electronic signatures (e.g. changes in various emissions, RF, transformers or power supplies and the like.

Behavior metrics or parameters relate to a behavior performed by a subject that can be used to discriminate the subject from another person. Behavior metrics may consist of one or more behaviors, actions, activities, motion speed, motion acceleration, motion velocity, direction of motion, general motion or activity, specific motion such as gestures or activity, hand gesture, a facial expression, a body position, eye blinking rate, number of eye blinks, body motion, a glyph, a vocal utterance, an aural utterance, motion of an object, position of an object, a drawn pattern, a time interval between two behavioral-metric inputs, physiological dimensions, induced vibrations, duration of a behavioral-metric input, a hand signature, hand signature elements, time elapsed for creating the hand signature or creating hand signature elements, a static gesture, one or more sign language letters, a rhythmic input, gait, motion, movement, positions, voice inflections, pressure, directions, steps taken during a predetermined time interval, step gestures, vocal sounds and/or utterances, motion and/or movements, brain activity, or any behavior and/or activity that can be sensed and is distinctive to the entity and/or the entity's "normal" and/or average behavior.

Psychological parameters may be collected from the subject's brain waves, including moods, interactions with others, thoughts, emotions, emotional intensity, attention, thought patterns, dizziness, depression, happiness, sadness, or any brain wave activity that can be sensed and is distinctive to the entity or to a knowledge metric.

Brain waves may also be sensed to detect an event or impending event. The brain wave sensors may include: alpha wave sensors, SQUIDS sensors, sensors especially sensitive in the near IR segment of the spectrum, sensors capable of measuring one or more of the frequency, amplitude, phase and power of brain wave signals. In one embodiment, a wearable device is placed near or touching an entity's head to collect brain waves only when in close proximity to the brain. In one embodiment brain waves are collected from the nervous system.

One or more of the sensors of the present system may be external to any operative communications system associated with the present invention. To this end, certain parameters or metrics may be detected by event detection devices external to an entity, but that pertain to the safety or well-being of the entity. For example, various metrics may be used to detect intrusion events including but not limited to physical access, door entry, motion detection, glass breaking, scream or shot detection and other access or safety indicators and the like. Other detection methods that could potentially detect an event specific to intrusion, or some other alarming event like an intruder or medical event such as stroke, includes but is not limited to sudden changes in heart rate, adrenalin, and/or brain wave activity, as non-limiting examples. In such events, an appropriate response may be to record sound and/or pictures, videos or multi-media from microphones and/or cameras on the local or other separate devices proximate to the entity.

Notification Server Versus Distributed

FIG. 1 illustrates a system 100 including one or more event detection devices 120. As shown certain embodiments comprise a storage element 110 as described below, while in other embodiments the storage element is not included nor required. In some embodiments that communicate (wirelessly in one embodiment) with one or more notifying devices 150 when an event has occurred. Notifying devices 150 can be centralized, in some embodiments, whereby alerts are sent to one or more servers locally or remotely to a server or on the cloud as non-limiting examples, or distributed, in other embodiments, whereby notifying devices 150 may also be combinations of features such as the event detection device 120 itself and/or the responding device (all contained in one). In the case where the system is a single device, detection, alerts, notification and response are all self-contained within the single device so that an entity is alerted and a response is performed locally when some event is detected on that same device.

Communications Methods

A communications link can be used to transfer collected and sensed data and information between the entity's various electronic and processing devices. Such a link can also be used to transfer an entity's personal data (such as health related information) to a caregiver or family member, either in real-time from the event detection devices and/or from a repository such as a portal or equivalent. In the latter case, for example, one's health can be monitored from afar by a family member or a medical professional.

Data such as but not limited to vitals, statistics, historical medical records, imagery, multi-media, reports and/or metrics collected over time may be viewed and managed from a central repository, or in some embodiments, distributed using decentralized database technology, or in some embodiments, via blockchain. The blockchain enables public release of medical data while keeping private data secure. Data may exist anywhere throughout a centralized or decentralized system, but only the owner of the data determines who has access to private data and when. For a non-limiting example, a doctor could be denied access after moving to another doctor. Data can be automatically copied or moved to another memory location or repository upon a change in permissions so that data is preserved while access change is honored. Data may also destroy itself, after validation of copying to another location, to further ensure integrity of the overall system. All data may remain encrypted via distributed key management, but data may be used to set parameters, thresholds and algorithms to detect events.

A device may include communications components to create a communications link to pass data and/or voice to send notifications, location, a two-way or multiparty audio link with another device over any communications channel according to one or more of the available communications protocols, e.g., Bluetooth, Bluetooth Low Energy, WiFi, NFC, LTE, 4G, 3G, EDGE, and RF over near field and/or extended distances, RF to a phone or a base station, RFID, a beacon signal, sound, light and the like. Additionally, a virtual intercom and/or "walkie talkie", push-button or otherwise, can be created between any two or more devices. In another embodiment, the wearable device of the invention communicates with a second device according to a single short distance protocol such as but not limited to NFC (near field communications). The second device may include multiple communications protocols for communicating with a plurality of different communications devices over varying distances.

Fall or Event Detection

In one embodiment in which the event detection device 120 (see FIG. 1) comprises a height detection device disposed in a pendant, bracelet or other wearable item, the height detection sensor determines height information from any one or more of height-determining devices (sensors) either embedded in the height detection device or separate therefrom. Although incorporating the height determining device into a wearable item may be most convenient, this configuration is not required so long as the person can gain access to the device when an emergency condition arises.

In the embodiment shown in FIG. 1, the event detection device 120 includes a floor height storage element 110 that stores a floor height (e.g., an altitude of the floor above sea level or a pressure above sea level at the floor height) at a location where the wearer is present. Before the wearer falls, a height of the event detection device 120 is outside a threshold range that would indicate the wearer has fallen.

When the wearer falls, the event detection device 120 detects this height change. If the device 120 remains within the threshold range of the floor (e.g., 8 to 16 inches from the floor) for longer than a predetermined period of time (e.g., 15 seconds), the device 120 sends an alarm signal to the notifying device 150, which may be located elsewhere in the space occupied by the wearer (e.g., a residence, home, apartment, condominium, assisted living apartment, assisted living facility, nursing home, hospital room, and boathouse).

In some embodiments, a second sensor, a motion and/or gyro sensor, may detect some movement and/or direction that may indicate a fall is about to take place. This event may in turn start or increase the rate of data collection or collect additional data by a second sensor that then uses pressure, as a non-limiting example, or another height detection sensor to detect the change in height. In some embodiments, the height detection sensor may or may not be worn by the entity. In addition to or in lieu of detection of height changes, the second sensor (or a third sensor) may collect other data from the entity that might be indicative of a fall or horizontal position, such as lying on a bed.

Where Worn

Various types of wearables can be used in conjunction with the invention to carry or enclose the sensors for collecting pertinent data. Such wearables may include: a wristband, bracelet, necklace, garment, ring, choker and the like to be worn on the head, face, wrist, arm, leg, foot or any part of the body, clothing or accessories.

Figure 2:
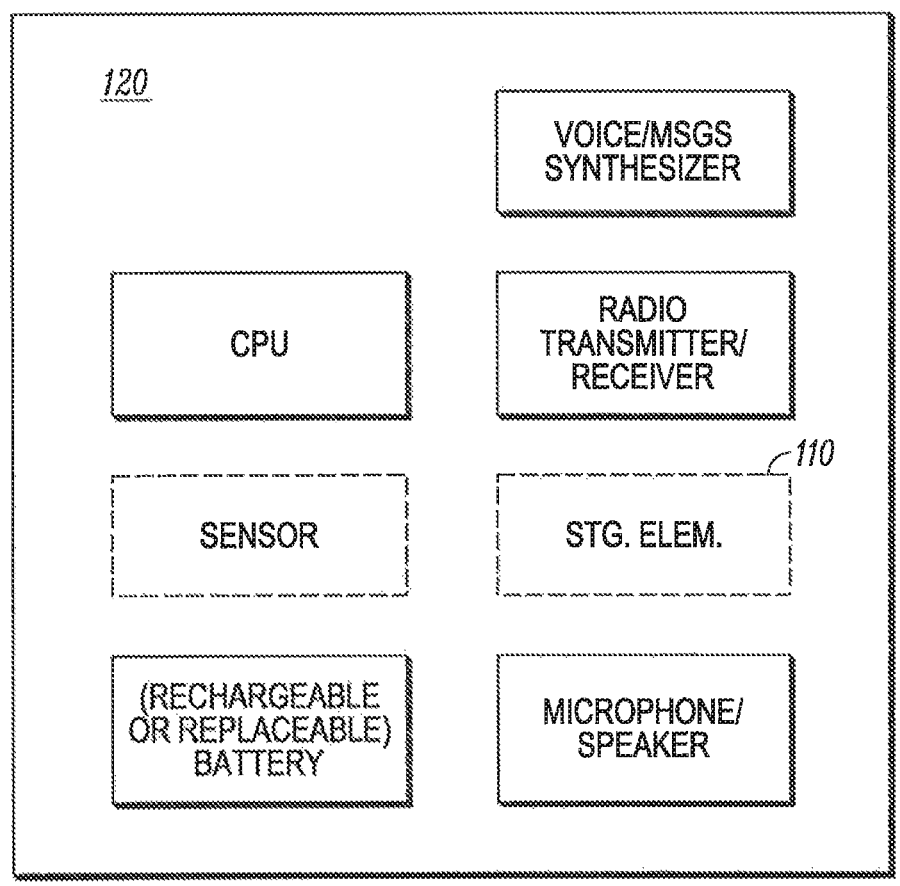
FIG. 2 is a block diagram of a height detection device of FIG. 1.

As shown in FIG. 2, in one embodiment the event detection device 120 comprises a battery-powered device that can be worn in a pocket, on a lanyard, on a wrist, clipped on a belt or worn on or as part of clothing, accessory and the like, for example. Although described in the context of a wearable, such is not necessarily required as various devices can be used to support the sensors, processors and ancillary components required in the context of the various embodiments of the present invention. For a non-limited example, sensors may be attached to a bed, a chair or some other object in certain applications.

Trigger Mechanisms and Physical Embodiments

In some embodiments, sensing devices may contain trigger mechanisms such as simple buttons and/or sensors that can send alerts to one or more other devices or social networks. In certain embodiments, event detection devices may take other forms such as attachments to beds, objects, embedded or hung on walls, accessories to other objects such as but not limited to wallets, keys or cell phones and the like. The device features could be part of and/or added to a mobile device, such as but not limited to a phone or phone case, wearable, or some other object. Likewise, the "alerting device" could contain sensors and/or manual methods such as a button, gesture, brain-wave detection sensor or the like to detect and event and facilitate an alert. In such embodiments, sensing and alerting combination devices may be clipped onto clothing, worn as jewelry or other wearable forms, or within inconspicuous forms such as buttons or other features on clothing, walls or other objects in general.

In some non-limiting embodiments, in lieu of or in addition to detection of an event responsive to sensed parameters, an event may be triggered by an entity "manually" or otherwise by purposeful intention. Methods to purposefully indicate the occurrence of an event and the subsequent issued alert include but are not limited to pressing a button, performing some gesture, behaving in some manner, or thinking a word, phrase, location, object or the like.

The event detection device 120 may include a battery (either replaceable/disposable or rechargeable, see FIG. 2), a sensor for gathering or receiving height-indicating information (and location information in one embodiment), a microprocessor (labeled as "CPU" in FIG. 2), a radio transmitter/receiver, the floor height storage element 110 (for storing a floor height in the embodiment where the event to be detected is a fall), and a microphone/speaker.

In certain embodiments and when using certain sensors, the event detection device 120 determines an absolute height, such as an absolute altitude above sea level. The absolute altitude, which may be derived from an atmospheric pressure measurement, indicates a height of the floor surface, and the value may be stored in the floor height storage element 110, including periodically as elevation changes.

Under certain circumstances, periodically (e.g., every 15 seconds) the sensor determines its height, i.e., an absolute altitude above sea level. Since the sensor is within the device 120, which is worn by the user, the altitude of the sensor is indicative of the altitude of the device 120 which is further indicative of the height of the wearer or user.

The system next determines (again periodically) a height difference (in one embodiment as indicated by a pressure difference) between the floor height value as stored in the floor height storage element 110 and the current height value (of the event detection device 120) as measured by the sensor. This difference value indicates the height of the device 120 above the floor or above the floor height.

Finally, this difference height value is compared with a threshold value to determine whether the wearer has fallen. A comparator, such as a logic circuit or a CPU and software, can perform this comparison operation. The alarm is issued to the notifying device 150 if the difference height value is within the threshold, as this indicates that the user has fallen.

Exemplary sensors for use in the system include but are not limited to: (1) an altitude sensor, (2) a GNSS (global navigation satellite system) sensor, (3) an RF sensor such as such as LTE, GSM, Bluetooth or WiFi sensor (4) a pulse oximetry sensor (5) a motion sensor (6) a light sensor and/or (8) a sonic or ultrasonic sensor. Combinations or all of these sensors may be used to determine the occurrence of a fall or incapacitated event. The use of these sensors is described in additional detail herein.

One embodiment uses a GNSS sensor to detect a fall. In a first technique, a GNSS sensor provides an absolute altitude. In a second technique, the GNSS sensor provides a relative altitude, e.g., relative with respect to another GNSS sensor such as a reference sensor 130 (which is at a known height).

In one embodiment, when the event detection device 120 detects a 'fallen' condition, as a non-limiting example, an audio link is opened with the microphone/speaker within the event detection device 120. The audio link may be established automatically upon detection of a fall, triggered automatically, periodically, or in some embodiments, initiated by another responding device. In addition to activating the microphone/speaker, other components of the event detection device 120 can be activated for receiving or determining/sensing information that can be used to negate the fall determination.

Once the audio link is established, the entity can be queried, such as by asking, "Are you okay? Have you fallen?" Such messages may be generated from the voice message synthesizer and heard by the wearer by operation of the microphone/speaker in the event detection device 120. The audio query message may be in the form of synthesized speech phrase stored within the voice message synthesizer.

Alternatively, an illuminated indicator (an illuminated lamp, for example) on the event detection device 120 may be energized to serve as the query. The query may also be issued by a Siri-like device in close proximity to the entity.

If no response is received from the entity or a response indicative of an emergency condition (e.g., a yelling response, a recognizable phrase such as "yes, I have fallen" or a moaning response, as non-limiting examples) is received, the height detection device issues the alarm to the notifying device 150, which in turn issues the notification.

In one embodiment the event detection device 120 and the notifying device 150 periodically exchange heartbeat signals to ensure that both devices are operable. Thus, in this embodiment if either device has not received one or more of the heartbeat signals from the other, the audio link is established with the wearer to again query the wearer as to his/her condition.

The microphone/speaker in the event detection device 120 (see FIG. 2), may be the preferred approach for the wearer, now designated as a fallen entity, to provide additional information as to her/his condition. This information can be forwarded for use by emergency personnel or any entity who will render emergency assistance, either in person or via a recording of the response for later retrieval and use by responding parties. Examples of this additional information may include, for example, "I slipped in the bathtub", "I fell down the stairs", etc., as non-limiting examples. Again, these specific details may be useful for anyone providing assistance to the fallen person. Any such additional information can be provided by the fallen entity directly to the microphone/speaker on the notifying device 150 for in turn communicating to anyone on the notification list or can be provided to the microphone/speaker on the event detection device 120 for communicating to the notifying device 150 and then to one or more parties on the notification list. The spoken words of the wearer can also be recorded and stored for later use.

The fallen entity may also cancel the initial indication of an emergency condition, again through the audio link with the microphone/speaker of the event detection device 120. For example, in response to a query or independent of a query, the fallen person can simply say, "Cancel", "no", or "I did not fall", all of which may be prompts or programmable as non-limiting examples.

To avoid false alarms, after conditions indicating an event was detected, but before the notification is issued by the event detection device 120, a confirmation query may be issued to the entity, as a non-limiting example. The query, which may be issued by the event detection device 120 or from a portal to be described in conjunction with FIG. 4, prompts the entity's response that may confirm the event (a fall, medical, safety or other emergency condition) or set aside the event as incorrect. If the wearer confirms the event, the notifying device 150 issues the notification; if the event is deemed incorrect, the notification is not issued. The entity's response may be pressing a button, gesture, in text form or vocal. If the latter, the vocal response may be checked for authenticity by voice recognition to ensure that the denial was issued by the entity of the event detection device.

Queries by be in the form of symbols, written text, banners, and/or audible alerts. Audible sounds may, in some embodiments include sounds, canned or synthetic words, and/or words or phrases in the voice of someone the entity knows. Queries may also include actual pre-recorded voice and/or video or multi-media "snippets" so that the entity is familiar with the voice and words or phrase that is being said. In yet other embodiments, TTS (text2speech) and STT (Speech2Text) may also be used to communicate with the entity.

After a fall or another emergency condition is determined and confirmed, the event detection device 120 issues an alert and the notifying device then issues the notification. In one embodiment, the system is configured to allot a revocation time interval for cancellation of the alarm or cancellation of the notification by the wearer. In the event the notification has already been issues, it is "withdrawn" or cancelled when the notifying device 150 issues a "cancel" notice. This revocation time interval is variable as set by the entity.

In another embodiment the event detection device 120 comprises a manual button or actuator for use by the entity to initiate or cancel the emergency condition. In an embodiment comprising two actuators, actuation of a first actuator confirms the emergency condition and actuation of the second actuator cancels notifications of the emergency condition. The length of time an actuator is held, such as a press and hold for some determined seconds, may also serve to cancel an alert notification.

Although a verbal confirmation from the wearer that he/she did not fall is preferred, in one embodiment the system comprises additional sensors for collecting medical and health parameters and vital signs (referred to as non-verbal parameters or metrics) that can be used to determine the entity's condition, including but not limited to an indication that a fall has occurred or did not occur.

To more accurately determine the fallen entity's condition, the event detection device 120 may include the necessary sensors to determine one or more of the following parameters: pulse rate, blood pressure, oxygen level, alcohol level, activity level, dizziness, steps taken during a time interval, behavioral changes, gait, scent, sweat, voice, blood chemistry art rhythms, EKG, cardiac and lung sounds, weight, body mass index, caloric intake, medications taken (time of administration, dosage), etc. These sensors can be activated concurrently or in a hierarchical fashion based on results obtained from other sensors. The entity can also provide additional information as to the condition through the audio link.

Certain of these conditions and parameters may also be captured by video and audio sensing and recording devices within the device 120, the device 150, or another component of the system. For example, a loud thump detected by an audio sensor may indicate that the wearer has fallen. Fusing the response from multiple sensors such as a microphone, for instance, with other sensors such as motions sensors and/or height sensors can help differentiate an actual fall event from false alarms.

Certain states and statuses of the height detection device 120 (and the notification device 150 and other devices associated with the present invention) may comprise one or more indicators (e.g., LEDs) on an external surface thereof. These indicators can indicate available battery power, charging status, on or off condition, connectivity to other devices in the system, errors, faults, etc.

Notifying Device 150

The principal function of the notifying device 150 is to issue notifications to various parties in response to the alarm signal issued by the event detection device 120.

The notifying device 150 can be located anywhere proximate and within communication range of the event detection device 120 (see FIG. 1) or can be incorporated into the event detection device 120 (not shown), or in yet other embodiments, be cloud based whereby a server or other notification device 150 has a communication path with the event detection device 120. In the former embodiment, the device 150 may sit on a shelf in the wearer's residence, be worn by the wearer, or be incorporated into a wall or wall-hanging, as non-limiting examples.

Figure 3:
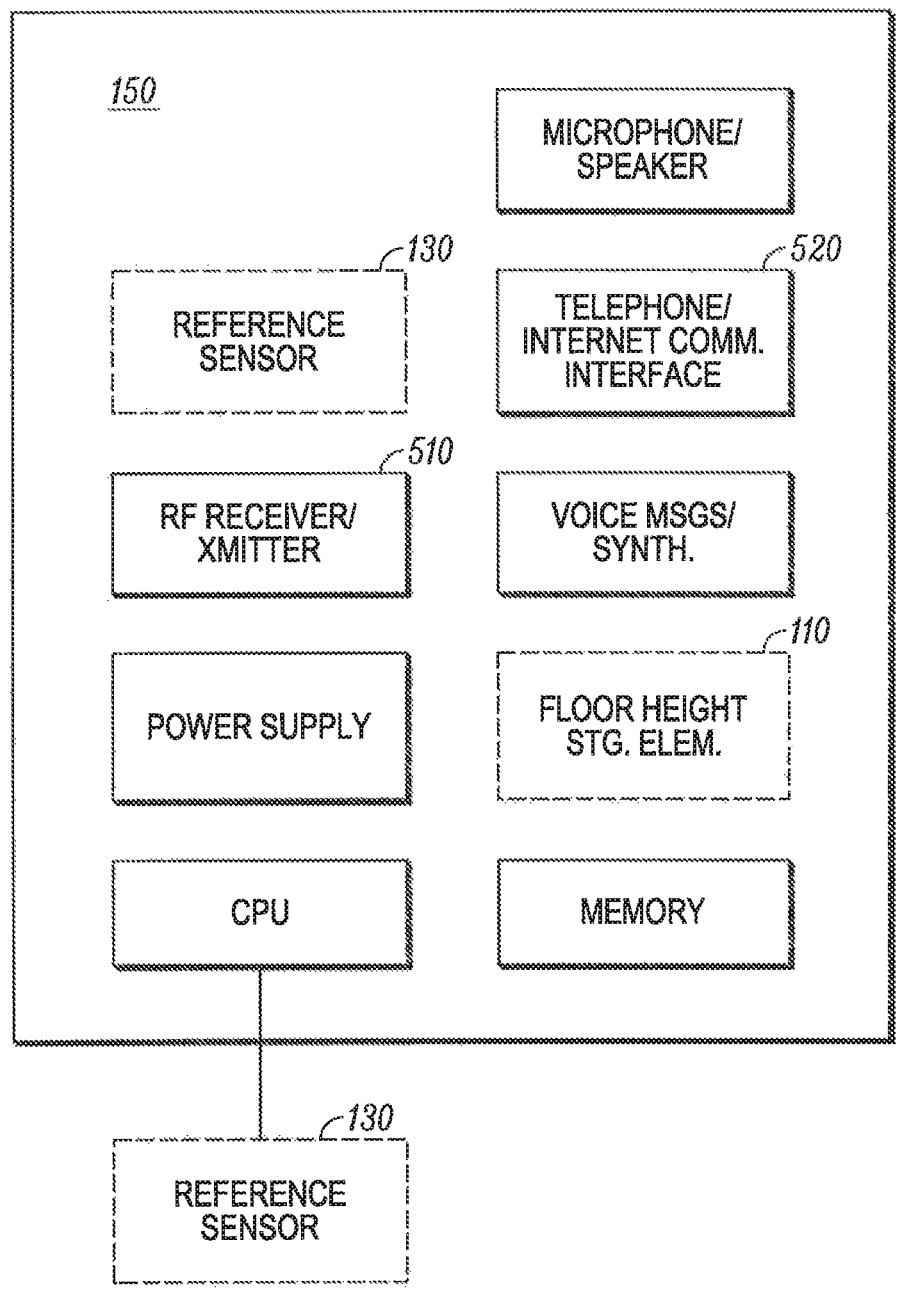
FIG. 3 is a block diagram of a notifying device of FIG. 1.

As shown in FIG. 3, the notifying device 150 may comprise one or more of an RF receiver/transmitter 510 for communicating with the height detection device 120, a power supply, a microprocessor/CPU, a telephone, and/or internet communications interface 520, a microphone, a speaker, and a voice message synthesizer.

In certain embodiments the device 150 further comprises a reference sensor 130 and the floor height storage element 110. In the latter case, with the floor height information stored in the notifying device 150, the device 150 participates in the fall detection process.

In yet other embodiment the device 150 may further comprise other sensors such as but not limited to a motion sensor, a direction sensor, a temperature sensor, a pressure sensor and/or a pulse oximetry sensor.

The power supply of FIG. 3 may comprise a transformer connected to a source of electricity. The power supply may additionally include (or may exclusively include) a battery-based power source for use when electricity unavailable. In some embodiments, the battery may be charged via a charging circuit connected to an external power source, such as USB, as a non-limiting example, and/or via power harvesting techniques such as but not limited to a solar panel, a piezo circuit and the like.

When the system has determined that an event such as a fall or falling asleep is immediately imminent or has occurred, the system can additionally contact a third party to come to the aid of the affected entity. Also, one or more communications channels may be established for use by the entity to speak with the third party. For example, a family member may be alerted, an ambulance and/or the police summoned, and/or the primary care physician contacted. A two-way voice channel may also be established between the entity and a third party, such as the family member, ambulance driver, medical professional and/or other entity.

Fall is only provided as a non-limiting example of the event detection system, and is not to be interpreted as the only event. A great number of events with varying alert levels can be detected for a great variety of responses include sleeping, getting out of bed, walking, running or exercise, missed medications, overdose, dizziness, dehydration, blood pressure and other metabolic changes, breathing changes, heart rate changes and the like.

A measurement, metric or parameter may also be performed outside of any event. In such cases, the vast number and variety of metrics and detected events may be utilized to form thresholds, algorithms and triggers to detect an event. In some embodiments, Artificial Intelligence (AI) is applied to adapt to the vast number and variety of data to formulate the criterion for an event. Thus, under this embodiment, AI adapts to the collection of metrics such as vital statistics to better prevent, diagnose and detect when an event alert should be detected and notified, to whom, and with which location and/or alert level or classification.

Events may also consist of predictions as well as actual occurrences. In this context, vitals and other metrics may include psychological metrics derived from brain-waves and other methods to sense emotional stability for the prevention of depression and/or suicides, as non-limiting examples.

The notifying device initiates outbound communications to a third-party through the appropriate communications interface 520 to issue a notification signal. Such an interface may include, but is not limited to, any one or a combination of communications devices such as: a PSTN telephone device, a cellular telephone device, a cellular texting device, and/or an internet and/or internet of things (IoT) communications device (e.g., an IoT device, a Bluetooth or BLE device, a WiFi device, VoIP device, an email device, or an instant messaging device).

As used herein, a third-party is any person contacted by the notifying device 150, including, but not limited to one or more 911 emergency services, a monitoring service, a doctor's office, a nurse's station, a social network, a chat room, a crisis or call center such as but not limited to an assisted living facility or hospital emergency/assistance desk, a friend or a relative. Other third-party personnel are described relative to other embodiments and applications of the present invention.

In some embodiments, no notification is sent, but rather a voice call is immediately established.

The notifying device 150 may include, in addition to or instead of the communications interface device 520, an audible sound generator, triggered by the alarm signal from the event detection device 120. The sound generator creates and emits an aural signal to those within hearing range of the notifying device 150. Likewise, a visible signal may be triggered from the event detection device 120. The actual alarm may be local to a device, or separate on another device called an "alarm device" henceforth.

The notifying device 150, through the communications interface 520, attempts to contact help responsive to the alert signal. The device 150 may make one or more attempts to locate a family member, crisis or call center, neighbor, front desk personnel, caretaker, central monitoring station, or the 911 emergency operator and the like. When contact is made, the notifying device 150 provides an indication of the problem (e.g., an LED, a message, a display, using recorded or synthesized speech, such as from a voice messages synthesizer shown in FIG. 3) or using another audio or digital message or signal.

The notifying device 150 may make VOIP or other connections, or dial numbers or otherwise attempt to contact help either in a pre-programmed "roll-over" order or in an order specified by the wearer during configuration of the system. Contact information for the parties to be contacted is stored within a memory of the notifying device 150, and calls may be escalated by the responder and/or the entity associated with the detected event at any time.

Likewise, in some embodiments, no notification is sent, but rather an actual voice call is initiated. A voice call may be performed over any communication path utilizing CODECs that help manage a call over low bandwidth communication paths, or via an actual dialed number. In all embodiments, contact lists may be utilized to notify and/or call all parties at once, or in hierarchical fashion where the notification and/or call is "rolled-over" to the next entity or group on the list after no response for some time period. Time periods for roll-over may be programmable via a setting.

In some embodiments, the call list may be remotely programmable over-the-air. For a non-limiting example, phone numbers on a SIM card could be remotely update over-the-air such that the roll-over numbers to crisis centers could be changed, similar to speed dial features in phones. The number of minutes could be unlimited or limited, depending on use case.

Sleep State

According to one embodiment of the system, the event detection device 120 and the notifying device 150 remain in a low power state until certain conditions occur. Maintaining the devices 120 and 150 in such a low power state obviously conserves battery power.

Various triggers are employed to "wake up" one or both of the devices 120 and 150. For a non-limiting example, the event detection device 120 can be automatically awakened periodically (every 10 minutes, for example) to determine its height relative to the floor reference height and determine if the height differential is within or outside the threshold range. If the differential is outside the range, indicating the wearer has not fallen, the event detection device 120 returns to the sleep state. If the differential is within the threshold range, indicating the wearer has fallen, the device 120, and the notifying device 150, transition to an operating state.

In addition to awakening the height detector, other sensors associated with the event detection device 120 can be awakened by a wake-up trigger.

According to another embodiment, the system of the invention further comprises an accelerometer that can sense motion of the entity and/or a gyro that detects several different directions. If such motion is sensed, a signal is generated to wake up the height detection device 120 from its sleep state. Once awakened, the device 120 determines whether a "fall" has occurred as described herein and if is detected, generates the alert signal to the notifying device 150, which in turn provides a notification to various parties as also described herein.

A motion sensor such as but not limited to an accelerometer and/or gyro and/or combinations of motion sensors can also detect motion or activity of the wearer. The frequency at which the event detection device 120 measures the pressures to detect a fall is responsive to such activity. That is, whenever the motion sensor first detects motion after a quiet period the device 120 is awakened and pressure readings are taken. The frequency at which additional pressure readings are taken is responsive to the activity of the wearer, as determined by the motion sensor. For example, the motion sensor can detect when the wearer is walking. Since walking increases the likelihood of a fall, the event detection device 120 can increase the frequency of height measurements during a walking episode. On the contrary, after a period of no activity as detected by the accelerometer (for example, the entity may be asleep) the rate at which height detection measurements are taken is reduced. Thus, the rate at which the height detection measurements are taken is throttled by the activity of the wearer.

Severity Level of the Emergency or Event

According to one embodiment, a severity level is assigned to a detected emergency event condition. The severity levels characterize the emergency and may be designated red, yellow, and green, or any other indicators, words or symbols. Clearly a fall is assigned a "red" severity level. When the event detection device 120 detects a fall, it is immediately assigned a "red" level. Other equally severe events may be assigned a "red" level, while less severe events are assigned to the "yellow" and "green" levels.

The severity level is determined by the event detection device 120 either from a verbal message of the wearer or from metrics derived by sensors, apart from the sensors that determine a fall condition. A signal indicative of the severity level is sent to the notifying device 150, which in turn issues notifications responsive to the indicated severity level. The specific details of those notifications as related to the severity level include: the communications vehicle by which the notifications are sent, the parties to whom the notifications are sent, and an indication of the immediacy of the condition (e.g., need immediate help for a fall condition or can wait a few days for scheduling the doctor's appointment).

Severity levels can also be changed (upgraded or downgraded) based on later observed metrics. For example, a yellow severity indicator based on an elevated blood glucose reading for an extended period may trigger an appointment request to check the medication type and dosage with a physician. But if the blood glucose level suddenly rises above a threshold value, the severity level is changed to red to trigger a "red" notification for immediate response by a family member or caregiver.

Notified Parties

Responsive to the alert from the event detection device 120, the notifying device 150 issues a notification to one or more individuals on a preconfigured list of persons to contact in case of an emergency (referred to herein as a "notification list"). The list may include friends, emergency personnel, family members, a chat group, caretaker, physician, emergency operator, police office, fire fighter, 911 operator, etc. All parties receiving a notification are also advised of the severity of the situation according to a red, yellow, or green indicator.

The notifying device 150 can communicate over one or more different communications channels and according to several different communications protocols to provide notifications to the one or more persons or groups. Generally, and by way of example only, the notification from the notifying device 150 to the one or more persons may take the form of a text message, an email, an instant message, messages to a chat forum, or any other electronic notification.

In addition to conventional communications protocols and techniques described herein, a device of the invention may also be used in the email and text message space and to conduct a transaction. The device can send and receive emails, push notifications and text messages, and/or any other alert or notification services, to provide time-based or location-based notifications to the user and activate a personal response to an email or a text message. Additionally, the device can store any of the data collected and transmit that data to another processing or analysis device.

The first party who accepts a notification initiates a voice call and is dubbed the "first responder." The first responder also has the capability to add other parties to the call. As a non-limiting example, if the initial notification is made to a son and a daughter of the fallen person and the son is first to accept the notification, the son becomes the "first responder." The son may want to add his sister to the call. Likewise, in other embodiments, other individuals may be added who did not receive the notification, such as a general practice physician, specialist or 911 dispatcher, as non-limiting examples. In yet other embodiments, one or more other individuals may request to be added to a call by notifying the first responder, who may then add or refuse to add the requesting individual. In this way, multiple parties may participate in the call to assist the fallen person and offer advice to anyone who is physically present with the fallen person. If an emergency personnel is deemed the first responder, he or she may opt to call other parties and/or receive calls from other emergency responders to join the call with the fallen person. If a medical professional is "in charge" she may opt to call other family members, medical specialists or other medical or emergency personnel.

All subsequently contacted and/or notified parties are informed of the "in charge" party and each is notified as to the party(ies) who have been contacted, parties who are currently "on the call", status information of the fallen party, and the like.

In addition, issuing the notification can open an audio link to the microphone/speaker in the event detection device 120 worn by the wearer, thereby allowing the wearer to speak directly with one or more of the notified persons. The fallen party can also participate in the call through a Siri-like device that has been integrated into the system.

All calls established responsive to an alert notification signal can be configured as two-way (person-to-person) calls or 3-way or multi-person calls (conference calls). Any party on a notification call can establish or request a conference call to add other parties to the call.

Video calls and video conferences can be used in lieu of or in addition to the audio calls referred to herein.

Alert Classifications

In another embodiment, if specific information about the wearers' condition can be determined, parties who were previously identified at the time of call set-up may receive the initial emergency call or may be later added to the call. In this case, the emergency is classified as to type, e.g., is it of a medical or safety nature. If the emergency is classified as a medical situation, then medical personnel are notified.

If the emergency is classified as a safety issue, then police assistance would be required and the notification and/or call would be routed to the appropriate alert management social network, group and/or crisis center. In such an embodiment the event detection device 120 may further comprise a plurality of actuators (e.g., manual buttons or switches, icons on a touch screen) each associated with a specific condition. A first actuator is associated with a fall condition, a second actuator is associated with chest pain condition, and a third actuator is associated with a request for groceries. By actuating the first or second actuators the wearer can summon medical personnel; by actuating the third actuator the wearer can summon help from a child or caretaker.

Additionally, the emergency condition can be classified as to its severity (red, yellow, or green)—is help required immediately or within 24 hours? This information can be provided orally by the wearer, by selection of the appropriate actuator on the device 120, by selection of the proper icon on a display or by preselection as to the action required based on the classification of the event. The severity can also be determined (and the appropriate color identified) automatically by the event detection device 120 and/or the notifying device 150.

Notification List

In another embodiment, upon receipt of the alarm signal, the notification list of parties (in effect, a distribution list) to be contacted had been prioritized such that the entity or party(s) at the top of the list is contacted first followed by contacting parties of decreasing priority on the notification list. Failing to reach the top priority party, the second party on the list is next contacted, and so on. Alternatively, in some embodiments the notification list may comprise a flat list, with all parties having equal priority or all parties contacted simultaneously.

In one embodiment, the list that is sent is responsive to the type, classification and/or level of the alert.

In another embodiment the first call is placed to a service provider, who then makes subsequent calls to family members, physicians, etc.

Details of the calling process, parties on the notification list, calling priority, type of notification, etc. are established when the system is set-up or configured.

Social Network

Utilizing one or more of the communication methods discussed herein, two or more entities may form a social network that maintains an ad hoc monitoring and/or management (via one or more event detection devices 120) of an entity, object or physical space. This social network could be formed as a result of an alert, dedicated to emergency response or one that supports personal monitoring, or augmenting an existing network that may or may not be expressly formed for the purpose of management and monitoring of one or more entities. In some embodiments, members of the social network may create or select topics, tasks, subjects or "threads" to segment conversations regarding the management of one or more entities.

For a non-limiting example, two or more responder devices, such as but not limited to cell phones, could be utilized to communicate with one another via software, app, browser or the like to manage the health and safety specific entity or area.

In some embodiments, the sensing and communicating devices may be part of a network or an Internet of Things (IOT). In other embodiments, the social network includes or comprises one or more crisis or call centers who take on the responsibility to manage the alerts. Regardless of the component that forms the social network, the social network that acts "responders" responsive to an alert notification is called an "alert management social network" hereafter.

In addition to alert management, such alert management social networks can be used to collaborate regarding the management of an entity, such as but not limited to discussing treatment, issues with medication, blood sugar or other changes in vitals, scheduling matters, sharing information such as files, imager, vitals, multimedia and the like. With the popularity of social media today, a user of the device of the present invention may choose to engage in "fitness", "happiness" (e.g. psychological, etc.) and/or "health" competitions with other social media users. Alert functions may also be added to such existing or new social networks, or in some embodiments, a social care network formed for the purpose of collaborating care for one or more entities. The user's physical actions can be sensed and tracked, as well as her/his physiological (biometric) metrics and/or psychological metrics. The physical action and biometric metrics can be collected by or uploaded to a social media website where they are compared with other social media users to determine who is the "fittest", "happiest" and/or "healthiest".

Data from either the event or collected metrics may be shared amongst the social network can be centralized or distributed via cloud, point 2 point or peer-to-peer (P2P) connectivity.

In one embodiment the notification process itself creates a chat room or social network, also referred to herein as a private healthcare social network. Within this embodiment of the invention, all interested parties may join the chat room upon receiving an alert notification. The "first responder", the first to accept the notification, may also invite others to join the chat room. All participants in the chat room are aware of all activities, medical information, medical test results, diagnosis, data associated with the fallen party, the severity level of the emergency (e.g., red, yellow, or green), etc.

The chat room/social network participants may share information with all members of the chat group in real-time through audio, video, messaging, and posting techniques. All participants in the chat room converse with all others in the chat room in the same conversation and each participant can invite others to join the chat room. The participants may be connected via a shared internet connection (according to the internet protocol standard or VOIP) or another similar connection. Additionally, chat room participants can share files and videos. Further, any chat room text message can be converted to a voice mail message, by operation of a speech to text converter, for the convenience of any party who does not have access to text messages, including the fallen party. All text messages, shared files, voice messages, etc. that occur within the chat room are recorded for later use and analysis.

The chat room participants are each provided with substantial additional information about the history and current condition relative to the detected event. By way of example only, this information can comprise: pulse rate, blood pressure, oxygen level, alcohol level, activity level, dizziness, steps taken during a time interval, behavioral changes, gait, scent, sweat, voice, blood chemistry art rhythms, EKG, cardiac and lung sounds, weight, body mass index, caloric intake, medications taken (time of administration, dosage), etc. Certain information listed above is obtained from medical sensors that provide real-time data. Other information is obtained from those individuals with close personal contact with the fallen party (e.g., information regarding exercise regimens, sleep patterns, and psychological observations). Still other information is obtained from historical medical records. With this considerable additional information, the chat room participants can make better informed decisions regarding the care and treatment of the fallen party.

Notification Via an "App"

Figure 4:
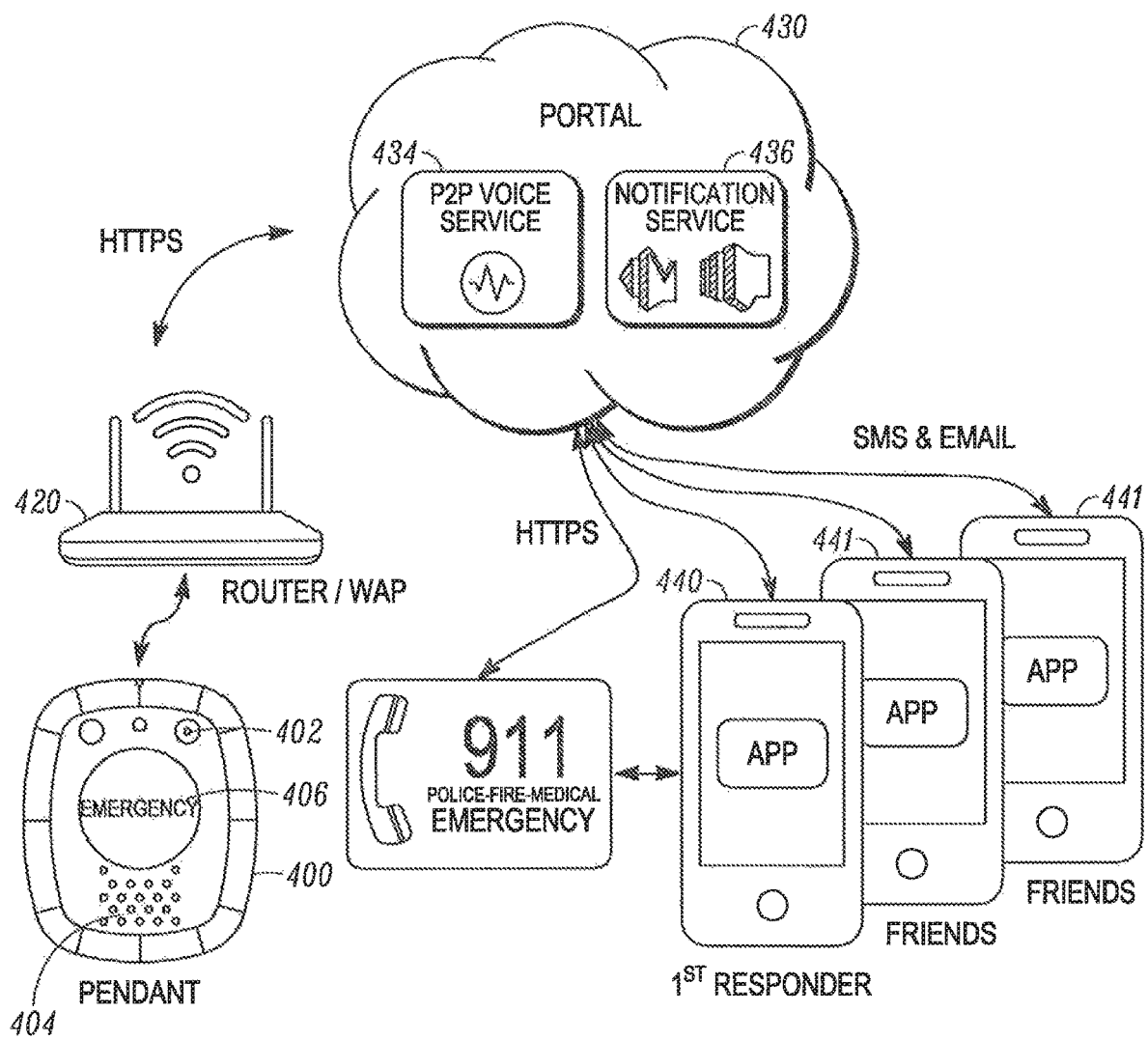
FIG. 4 is a block diagram of an event detection system of another embodiment of the invention.

The system of the invention can also be embodied in an application (colloquially referred to as an "app") executing on a personnel electronic device, e.g., a mobile phone, iPad, laptop and the like as well as a wearable item. The app-based embodiment is illustrated in FIG. 4.

A pendant 400 functions in a similar manner to the event detection device 120. A microphone 402, a speaker 404 and an emergency button 406 are illustrated. The emergency button 406 can be activated by the wearer in the event of an emergency, for example if the wearer is unable to speak or if an emergency that has not been detected by the pendant occurs.

According to one embodiment the pendant 400 communicates bi-directionally with a WiFi router 420 (also referred to as a wireless access point), that in turn communicates with devices within a cloud-based portal 430 over an HTTPS link.

A P2P (peer-to-peer) voice service 434 sets up and controls communications with the parties who have received the notification, and a notification service 436 issues the notifications.

The portal 430 (more specifically devices and functionality within the cloud) communicates with a first responder's personal device 440 and personal devices 441 of other friends, family, and healthcare providers. As illustrated the first responder can contact the 911 emergency services or this can be done directly by the notification service 436.

The devices 434 and 436 also control and set up devices participating in the chat room and control communications among chat room participants.

A touch screen present on any of the devices 440 can present icons that are used to perform the various functions described herein.

When a fall is detected or surmised, a query signal is sent from the event detection device 120 (or another event or fall detection device not illustrated in FIG. 4) to the pendant 400 via the wireless router 420. The alarm signal issued by the pendant 400 when a fall has been detected (and confirmed in one embodiment) is sent from the pendant to the wireless access point and then to devices in the cloud.

The communications protocols indicated in FIG. 4 are merely examples of protocols that can be used with the present invention.

Returning to the system 100 of FIG. 1, the system 100 can determine the difference between a wearer lying down on a sofa for a nap and lying on the floor. Thus, the wearer can wear the event detection device 120 all day and night if desired.

During set-up, one of the interface controls is activated to command the event detection device 120, which is at floor level, to determine its height and store this value in the floor height storage element 110. Such a command is received by the radio transmitter/receiver in the event detection device 120.

As discussed above, the sensor element of the event detection device 120 can comprise any sensor capable of determining the current height of the device 120. Certain sensors are accurate within one foot. One embodiment employs an altitude sensor to determine the height of the height detection device 120. An absolute pressure sensor (altimeter) can be used to determine absolute height or altitude based on pressure changes relative to altitude. Techniques for performing these operations are known by those skilled in the art.

While certain sensors may drift with environmental changes (e.g., temperature and humidity), such changes can be compensated by using a reference sensor 130 (see FIG. 3) in a fixed position and/or for providing reference measurements (e.g., relative altitude, temperature, and/or humidity). Accordingly, changes in environmental conditions that affect the height measurement can be compensated with reference measurements supplied by the reference sensor.

In any of the described embodiments employing voice communications, the microphone/speaker must be appropriately sized responsive to an acoustical signal strength of the spoken words (for the microphone) and for the generated acoustic signal (for the speaker). Given these constraints certain embodiments may use a separate microphone and speaker, in lieu of one acoustic transducer that performs both functions. Physical size, current demand, available power sources, separate components or a single dual function component must be considered relative to the preferred size of the event detection device 120/580.

In yet a further configuration, the event detection device 120 and the notifying device 150 are integrated in a single enclosure such that the device 120 can issue a notification when an emergency condition is detected. In such an embodiment, the device 120 can communicate and issue notifications according to any communications protocol over any communications channel. Such a configuration may further provide the transmission of voice to the third party, as described above.

Figure 5:
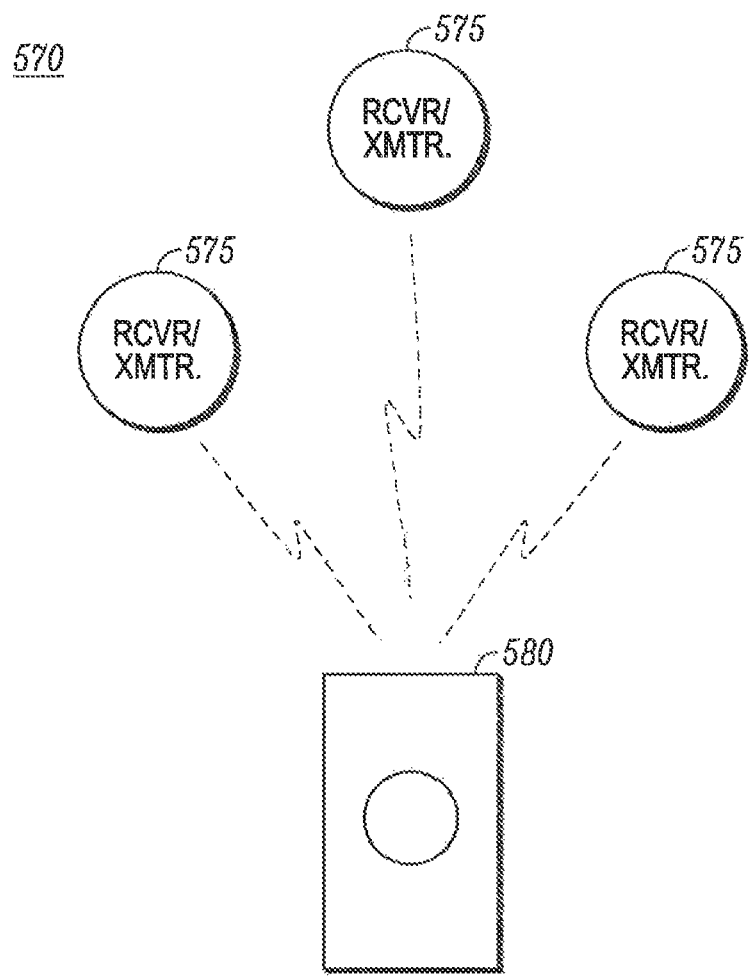
FIG. 5 is a block diagram of a triangulation-based event detector.

GSM, Bluetooth and WiFi detection systems may also be used for detecting height by monitoring a signal strength of a signal received from several known location transmitters. As shown in FIG. 5, in a system 570 transmitters/receivers 575 are at known transmitting locations, the known location transmitters 575 emit a signal that an event detection device 580 uses to triangulate its height and/or position. Although described in conjunction with height detection herein, the event detection device 580 can also detect other "events" as described herein.

In a configuration where the receivers of the transmitter/receiver 575 are at known locations, the known location receivers 575 receive a signal from the height detection device 580 that can use be used to triangulate its height and/or position.

Typically, in either case such triangulation is performed by triangulation circuitry by measuring signal strength from the known location transmitters and/or receivers 575 and/or arrival times of signals at either the event detection device 580 or at the location transmitters and/or receivers 575. The received information also can be compared with information based on a previously generated map of the signal strengths at different points.

The event detection device 580 and the known location transmitters and/or receivers 575 may also use bidirectional communication to determine position of the event detection device 580 and thereby the location of the wearer. For example, when the known location transmitters and/or receivers 575 detect that the event detection device 580 has emitted a location signal, they each respond with their own reply signal. By measuring a response time from each of the known location transmitters and/or receivers 575, the event detection device 580 can determine its position.

Moreover, in a bidirectional communication embodiment, the transmission from the event detection device 580 to the known location transmitters and/or receivers 575 can utilize a first communication technique (e.g., RF) which the transmission from the known location transmitters and/or receivers 575 to the device 580 utilizes a second communication technique (e.g., ultrasound).

In the triangulation-based embodiments, the event detection device 580 includes a floor height storage element such that the device 580 can determine if the event detection device 580 is in a 'fallen' condition.

In yet another alternate embodiment, sonic and/or ultrasonic sensors may also be used for sensing a height relative to the floor. In one such embodiment, location transmitters and/or receivers 575 would be arranged in various locations within the living quarters of the wearer. The event detection device 580 emits a sonic or ultrasonic sound wave once every minute, for example, and the location transmitters and/or receivers 575 receive the signal.

Other sensor types can be used to detect a "fallen" condition. A piezoelectric material produces a voltage responsive to application of a force or pressure. In one embodiment a sensor comprising such material is placed at strategic body locations that would experience a force when the wearer is in prone position. The resulting generated voltage is used to indicate alone or conjunction with one or more other sensors, that the wearer has fallen.

A ball switch or tilt sensor, which generate a voltage when oriented at predetermined angles, can be used to indicate that the wearer's body is oriented at an angle that suggests she/he is not standing upright. The tilt sensor or ball switch can be used in conjunction with one or more additional sensors to confirm that wearer's orientation or can be used alone to determine a fallen condition. However, this approach may generate false alarms when the wearer is taking a nap or lying in the bathtub, for example.

A timer may be used with any of the various sensors described herein to distinguish the wearer's transient body orientations (she knelt down nearly prone to retrieve an article from the floor) from body orientations that persist for an extended period.

The event detection device 120 or 580 may further include at least one sensor to determine that it is being worn thereby reducing false alarms. One such sensor comprises a movement sensor indicating a worn condition when movement (even a slight movement) is detected or when several movements are detected within a specified period of time.

An alternative "worn" sensor comprises a pulse detector. When the event detection device 120/580 is worn as a wrist strap or belt device, the pulse sensor monitors the pulse of the wearer. The absence of a pulse indicates the device 120/580 is not attached to the wearer, thereby again avoiding false alarms.

A heat detecting sensor comprises yet another sensor for determining whether the device 120/580 is worn. In this configuration, the event detection device 120/580 is placed in contact with a region of the skin. The device measures a skin surface temperature to determine whether the temperature is within range of a typical human skin temperatures.

A sensor for detecting simple physical contact with the wearer's skin can also determine whether the event detection device 120/580 is worn.

In another embodiment designed to avoid false alarms, the system of 100/570 specifies 'safe areas' where the wearer can lie down without triggering an alarm. Such places may include a sofa, bed and bathtub. With sufficient accuracy to distinguish such locations in the wearer's living quarters, the wearer can assume a prone (lying down) position and avoid triggering an alarm signal. These safe areas can be established during system configuration.

With this safe area approach, a determined prone position within a safe zone does not generate an alarm signal, but a prone position outside of a safe area generates an alarm.

Event Detection Device

The event detection device 120 issues an alert responsive to certain conditions that indicate the person (or physical space) monitored by the device 120 (also referred to herein as a wearer or a fallen person) has experienced an event worthy of an alert, such as but not limited to a fall. In turn, the notifying device 150 notifies one or more persons of the detected condition.

Adaptive Sensing

In one embodiment the event detection device 120 monitors various values associated with a condition of the monitored entity. The values can be sensed or measured continuously, periodically, or adaptively. In the latter case, the adaptive sensing rate may be based on a simple time-of-day or day-of-week schedule and/or a complex interaction of several other parameters. For example, if the entity's body temperature, blood pressure and heart rate have all fallen, this may trigger more frequent data collection for a specific sensor type and/or conducting another sensing activity such as performing an EKG, as non-limiting examples. Furthermore, various parameters could predict a potential event, such as falling and/or falling asleep while driving as non-limiting examples, and an appropriate response could be performed either locally on the same local device, and/or another remote device to which the indicating data has been transferred.

Analyzed individually or aggregated, the various metrics and parameter values can invoke an appropriate response. For a non-limiting example, certain physiological parameters (e.g., blood pressure or heart rate) may be determined by a wearable device, which includes sensors. The sensed parameters are analyzed and may indicate the subject is about to fall or has fallen. A pressure sensor, accelerometer, gyroscope and/or combination of sensors worn by the entity (components of the wearable device in one example) may provide additional indicators that such a fall is imminent or has occurred. Likewise, sensed parameters could detect if a person is dizzy, about to fall asleep, or having a respiratory or cardiac event. In all examples, sensors worn by a person or external to a person such as image or sound sensors hung on a wall or embedded into an object could provide additional indicators that may be used to determine whether an emergency event is about to occur or has occurred, and alert one or more entities and/or devices to take appropriate response.

According to another embodiment, after a fall is detected but before the alarm is issued by the event detection device 120, a query is issued to the wearer. The query prompts the wearers response that may confirm the fall (or another emergency condition) or set aside the fall detection as incorrect. If the monitored person confirms the fall, the notifying device 150 issues the notification; if the event is deemed incorrect, the notification is not issued.

A detected event may be deemed incorrect by one or more of the following methods: sensors detect some criteria that reduces or eliminates the criteria required for a valid event, algorithms or thresholds deem the event no longer valid, timers and/or subsequent indicators deem the even invalid, and/or some response from the user indicating the event is no longer valid and should be canceled.

The event detection device 120 may contain one or more of the following sensing capabilities: height, movement, motion, blood sugar, blood pressure, pulse, pulse oximetry, temperature, sweat or any of the other parameters set forth herein.

The notifying device 150 may be a separate element from the event detection device 120 as illustrated in FIG. 1 or a component of the height detection device (not illustrated in FIG. 1). In another embodiment, the notifying device comprises an independent notification service in which case an event or alarm is issued to the service and the service issues one or more notifications.

Responses to an Event Detection

Responses or stimuli directed to an entity may include, but are not limited to, indicators, vibration, shock, sound, lights flashing and the like. Other indicators that can captures the attention of a person may include but are not limited to messages and/or voice calls from one or more responding entities and/or devices.

Data Fusion

The data analysis process may involve fusing two or more data collected from the sensors and/or previously collected data to improve the propriety of a desired response. These parameters can be compared to the same parameter of the entity measured at an earlier point in time or compared with a large population of entities to determine a normal parameter value and/or thresholds and/or patterns that may be used to detect events. In either case, if the analysis determines that a parameter value is within or outside a normal range and "event" is detected and a notification with subsequent associated response is triggered. The collected data can also be aggregated with data from other entities to determine if the parameter is within or outside some range and thereby trigger an associated response, such as the occurrence of an event for which assistance is required.

In some cases, the collected data is stored and later a historical analysis of data is performed. This analysis could provide trend information to the owner of the data, medical or fitness professionals, or shared with other individuals such as family or friends and the like. In some embodiments, data and/or data analysis may be shared over social media, or via apps on mobile, static and/or wearable devices.

To collect data (metrics or parameter values) to support detection of an event, the devices include appropriate sensors, such as physical sensors, brain wave sensors, transducers, pulse oximeters and the like. Such sensors can also be disposed on a wearable device. Other sensors are described elsewhere herein.

The use of various parameters for making certain decisions, performing certain actions, or detecting an event are described herein. However, it is recognized that certain parameters may be better indicators in conjunction with a specific decision or a specific action than other parameters. These "better indicators" can be regarded as a suite of indicators associated with that decision or action, and sensing and analyzing that suite of indicators can yield the most probable result. But such an approach does not suggest that the other indicators are of no value. However, these other indicators may not significantly improve the accuracy of the result and their analysis can therefore be avoided.

Some of the various described embodiments refer to the use of absolute parameter values for making a decision or performing an action. However, in certain embodiments, a change in one or more parameters (such as a sudden drop in blood pressure or a change in a behavior-metric and/or brain-wave metric) over a time interval may be more revealing than steady-state values and therefore trigger a desired response, e.g., detection of a health-related event.

Location

In certain embodiments and applications device location may be important. Device location may be derived with the same communications methods described herein or in some embodiments, with the addition of external positioning systems such as but not limited to GNSS (global navigation satellite system), GPS (global position system) and VLC (visible light communication), beacon or other RTLS (real-time location system) technologies so that location information can be sent by a device along with alerts.

A sensing device may additionally indicate its current location for the benefit of any responding parties and store all measured and sensed parameters (in particular biometric and/or behavior parameters) for later analysis and for use in predicting subsequent falls by the entity.

Certain techniques and devices are able to determine location indoors. For a non-limiting example, location of a sensing device may be derived utilizing beacons sent over Bluetooth or other RF (Radio Frequencies) so that the sensing device location may be derived derive its location. Another embodiment utilizes WiFi fingerprinting, a method that utilizes a set of WiFi signals captured by a mobile device and the measurements of received WiFi signal strengths (RSSs) from access points surrounding the device, thus deriving a "fingerprint" on a radio map of the correlated WiFi devices. Other methods utilize triangulation of cellular towers, TV towers, and other transmitters to derive location information, or in some embodiments, a location's lighting grid that forms a location-based positioning system utilizing visible light communication (VLC) technology.

Sensor Activation

Some described embodiments and applications involve a wearable (i.e., a wearable garment with various electron devices disposed therein or thereon). The wearable, including various buttons and/or sensors attached thereto or supported thereby, would be less intrusive than even a smart phone, but can offer a plurality of services to the wearer. The sensors can be activated based on time periods, time intervals, one or more entities entering or leaving a location or area, and/or manually such as placing one or more fingers in contact with or proximate a sensor, thereby activating the sensor to collect data.

Predictions/Algorithms

Certain systems of the present invention predict the occurrence of an event using applicable sensor data. Algorithms are employed to control and activate the various sensors and transducers and to analyze the sensed parameters in predicting or determining that the event (e.g., a fall, a seizure, falling asleep, a medical event, trauma and/or shock, etc.) will occur or has occurred.

Algorithms, executing in real-time or post-event, analyze the sensed data and information collected. As is known by those skilled in the art, these algorithms can be constructed to analyze all relevant data or subsets of that data to reach a conclusion. The algorithms can execute continuously or on a periodic basis, as well as locally and/or delegated and/or distributed to other entities and/or processors. Optimizing the algorithms may be desired depending on the nature of the action to be taken. For example, in the case of predicting a fall, nearly continuous monitoring, if not continuous monitoring, is preferred, while sleep and/or fitness analysis may only be performed when the activity of sleeping and/or exercise is detected.

Use of the system of the present invention to predict a fall may occur or declare that a fall has occurred, is one simple example of the many types of physical or health related situations that may be predicted or confirmed according to the present invention. Clearly, when considered relative to health situations, it is far better to predict the occurrence of a debilitating event than to confirm that such an event has occurred. Nevertheless, this invention covers both scenarios.

According to another embodiment, detecting that the subject has awakened (or the subject has fallen asleep) triggers the collection of certain sleep-related parameters. For example, parameters that indicate the subject is sleeping comfortably, e.g., lowered blood pressure and heart rate, can be collected after the device has determined that the subject has fallen asleep, thereby adapting data collection of one or more parameters to events detected by one or more other parameters.

Responses to Wake-Up Person

In a wearable or other application where a device is in close proximity to a person, an alert responsive to the event, is provided locally to the wearer of a wearable or person close to the device. Responses can may include but are not limited to vibration, shock, haptic feedback, sound, illumination of a visible-light or infrared LED, and/or another local response. In other embodiments, a second device, such as but not limited to a phone, is activated and the alert provided by indication on a display, vibration, seat or bed movement, audio sounds via a speaker, or ultrasonic signals.

Mood Detection

The biometric and/or behavior-metric data collected according to the present invention can also be used to rate the "fitness" of the user. Even a psychological indicator (such as a depressed or happy mood) can be incorporated into the algorithm that determines a user's physical fitness. Obviously the biometric and behavior-metric sensors will play an important role in determining fitness, as do thought activities measured by brain-wave analysis.

Other Purposes

In addition to using the sensed data to detect or predict an event, the data can be used for multiple other purposes as described below.

The sensed data can provide: access control; data transfer, storage, and analysis (such as medical records); data transfers between two devices or among a plurality of devices; transaction executions; notifications (aural and visual); alerts; emergency responses; 1 or 2-way communications with a third party such as a medical, professional and/or family or friend; modifications to exercise regimens, modifications to health regimens such as but not limited to check-ups, food or water intake, and the like Any one or more of the event detection mechanisms described herein, including sensed and/or measured parameters and/or metrics, may be used to authenticate an entity, before an entity is permitted to execute a transaction or gain access to a secure area or to a secure device. Any one or more of the many different known biometric, behavior metric, knowledge metric, electronic metric and/or brain wave metrics can be used to identify (authenticate) an individual and determine that she/he has been permitted to gain access to the system or the limited-access area. Different or additional biometric, behavior metric, knowledge metric, electronic metric and/or psychological metric parameters can be used depending on the level of security associated with the system or limited-access area.

In certain embodiments, multiple entities may be simultaneously authenticated based on collected data. Also, a single entity may be simultaneously authenticated to execute a plurality of alerts and/or transactions, or in some embodiments, given access to a plurality of secure areas and/or devices.

Like other devices of the present invention, a wearable or other sensing device may also be used to authenticate, monitor (health or fitness, for example), conduct transactions, transfer data, and/or control a device or system via brain waves, gestures, touch interfaces, or any measurable or determinable action.

In conjunction with its use to execute transactions, a device may make payments, place orders, redeem rewards, manage insurance and financial accounts, monitor credit scores, manage loyalty accounts, and the like. The device can also store the user's social security number and use it or a portion of it to conduct certain transactions if appropriate safeguards are in place. Certain wave patterns or a gesture, for example, may indicate the account to be paid or the amount to be paid, while also, in some embodiments, authentication of the entity making payment and/or authorizing payment and/or payment parameters, such as but not limited to the payment amount.

Caloric Intake

In an application where the sensed data relates to caloric intake, a device of the invention (including a wearable) may determine the type of food ingested, the amount of food ingested, and the content of the food ingested. These parameters can be used to determine the caloric intake. This caloric-intake information can be acquired from: manual entry by the user, analysis of imagery of the food, measuring the impedance of body tissue, spectroscopic analysis, and analysis of sounds, vibrations, and motion during eating.

Medication Services

Recognizing the importance of taking both prescription and non-prescription medications on schedule, a device of the present invention can determine the number of and types of pills ingested, and the time of day that the pills were taken. This information can be stored for later use and/or immediately transmitted to a third party for verification that the pills for the day have in fact been taken. Like other sensed parameters, this data can be correlated to schedules and/or other data collected in order to activate other measurements and/or actions.

Personalized Services and Medication Delivery Based on Alerts

Any one or more or a combination of sensed or measured parameters can be used to determine a personal preference of the subject and/or offer a "personalized services". For example, detecting a high blood sugar level may generate and present information (e.g., advertisements) to the subject relative to drugs and physical activity regimens to help lower that sugar level. Detecting a high blood sugar may also trigger an alarm to the subject, a member of his family, or his physician. Detecting a high sugar level may also initiate the ordering and delivery of insulin and syringes to the subject's residence or office.

In another embodiment, a sensed or measured parameter may indicate an entity's favorite food or drink, thereby triggering an advertisement responsive to the preference.

In another embodiment, the presence of the entity may be sensed and a personalized service promoted or an advertisement displayed. Additionally, personalized services or ads may be activated based on various triggers, including but not limited to an entity's activity, a timer, a specific time, or a time interval, a response to a query, a transaction, motion detected or specific motion detected such as walking, running, standing, driving, or sleeping.

When the user enters a retail establishment, as determined, for example, by GNSS and/or other location technique, certain parameters can be sensed or collected to determine a user's location within the establishment (e.g. aisle, counter, etc.), what the entity is observing, what the entity has purchased, etc.

Fitness

As related to fitness data, the device of the present invention can determine the number of visits the entity makes to a gym, spa, or another work-out facility. The length of time spent at the facility, the number of visits over a time interval, the exercise equipment used, and the duration of use of each exercise machine can be determined, stored, analyzed, and used to generate an historical picture of the subject's exercise regimen.

Co-Owned and Incorporated Applications

The following co-owned applications disclose and/or claim concepts relevant to the present invention and each is incorporated herein by reference in its entirety.

Sound-Directed or Behavior-Directed Method and System for Authenticating a User and Executing a Transaction, filed on Feb. 10, 2016 and assigned application Ser. No. 15/040,984.

Multi-Instance Shared Authentication (MISA) Method and System Prior to Data Access, filed on Jun. 23, 2016 and assigned application Ser. No. 15/191,456.

Biometric, Behavioral Metric, Knowledge-Metric, and Electronic-Metric Directed Authentication and Transaction Method and System, filed on Jul. 5, 2016, and assigned application Ser. No. 15/202,515.

Components for Enhancing or Augmenting Wearable Accessories by Adding Electronics Thereto, filed on Sep. 2, 2015, and assigned application Ser. No. 14/843,930.

Method and System to Organize and Manage Transactions, filed on Dec. 2, 2016, and assigned application Ser. No. 15/368,546.

System and Method to Personalize Products and Services, filed on Jul. 15, 2016, and assigned application Ser. No. 15/212,184.

System and Method to Personalize Products and Services, filed on Sep. 6, 2016, and assigned application Ser. No. 15/257,101.

System and Method to Determine User Preferences, filed on Jul. 15, 2016, and assigned application Ser. No. 15/212,163.

Preferences Driven Advertising Systems and Methods, filed on Jul. 15, 2016, and assigned application Ser. No. 15/212,161.

While certain configurations of structures have been illustrated for the purposes of presenting the basic structures of the present invention, one of ordinary skill in the art will appreciate that other variations are possible which would still fall within the scope of the appended claims.

What is claimed is:

1. A system for determining occurrence of an event and for issuing notifications responsive thereto, the system comprising:
   a first component for storing first and second reference parameter values for use in determining occurrence of the event;
   a first sensor for determining first real-time parameter values at time t1;
   a second sensor for determining second real-time parameter values at time t2, the second real-time parameters different from the first real-time parameters and time t2 after time t1;
   an analysis component for determining whether the first real-time parameter values exhibit a first relationship relative to first reference parameter values;
   responsive to the first relationship, the analysis component for determining whether the second real-time parameter values exhibit a second relationship relative to the second reference parameter values;
   a communications component for issuing a notification that an event has occurred responsive to the second relationship.

2. The system of claim 1 the analysis component determining that the event occurred and issuing an indication to the communications component that the event occurred, the communications component waiting a time delay before issuing the notification, wherein during the time delay issuance of the notification can be canceled by a user of the system.

3. The system of claim 1 for determining occurrence of an event related to a monitored person, wherein the monitored person can cancel a notification before or after the notification is issued.

4. The system of claim 1 for determining the occurrence of an event experienced by a person, the analysis component for determining that an event is impending and the notification provided to the person and to other entities as designated by the person.

5. The system of claim 1 the analysis component for determining the occurrence of the event as experienced by a person, the system further comprising a second component for confirming occurrence of the event by a verbal exchange with the person, the communications component for issuing the notification responsive to the analysis executed by the analysis component and confirmation by the second component.

6. The system of claim 1 comprising a wearable item worn by a user, wherein the first real-time parameters are determined based on a location of the user at time t1 and the second real-time parameters are determined based on a location of the user at time t2.

7. The system of claim 1 wherein the event comprises a fall, the system for determining that a user has fallen, further comprising the analysis component for analyzing trending of the first or second real-time parameter values to determine whether a user of the system has fallen.

8. The system of claim 1 for determining the occurrence of the event as experienced by a person, the system, further comprising an activity monitor for monitoring an activity level of the person, a frequency at which the first or the second sensor determines respective first and second real-time parameter values responsive to the activity monitor, wherein increased activity of the person, as indicated by the activity monitor, causes the first or the second sensor to determine respective first or second real-time parameter values more frequently and a decreased activity level of the person causes the first or the second sensor to determine respective first or second real-time parameter values less frequently.

9. The system of claim 1 the event comprising a health-related condition or a personal emergency situation.

10. The system of claim 9 the event comprising the health-related condition, the first and second reference parameter values, and the first and second real-time parameter values each comprising health-related parameter values.

11. The system of claim 1 the first or the second sensor enclosed within or disposed on an item worn by a person.

12. The system of claim 11 the item comprising a pendant or a wearable.

13. The system of claim 1 the event designated according to a severity the notification issued by the communications component to entities according to the severity and recipients of the notification determined according to the severity wherein the severity is determined based on a comparison of the first and second real-time parameter values and the first and second reference parameter values.

14. The system of claim 1 the event comprising a medical-related event or a safety-related event, recipients of the notification determined by whether the event comprises the medical-related event or the safety-related event.

15. The system of claim 1 further comprising a second component for determining that the first or second sensor is worn by or proximate a person monitored for the occurrence of the event.

16. The system of claim 1 the notification received on a personal electronic device of recipients designated responsive to the event.

17. The system of claim 1 an event-management social network established responsive to the notification.

18. The system of claim 1 the notification issued to a first person and if the first person does not respond to the notification after a predetermined roll-over time, the notification issued to a second person.

19. The system of claim 1 the notification comprising a vibration, a shock, a sound, a flashing light, a text message, a voice call, or an email message.

20. The system of claim 1 for determining an event of a monitored person, wherein the event comprises an event that occurs external to the monitored person.

21. The system of claim 1 the first or the second real-time parameter values comprising physical parameter values, psychological parameter values, and brain wave parameter values.

22. The system of claim 1 further comprising a query-issuing component for issuing a query related to the event prior to issuing the notification.

23. The system of claim 1 for determining an event of a monitored person, a location of the first and second sensor in physical contact with the monitored person or at a distance from the monitored person, such that in either location the first or second sensor determines respective first and second real-time parameter values.

24. A system for determining occurrence of an event and for issuing notifications responsive thereto, the system comprising:
- a first component for storing first and second reference parameter values both for use in determining occurrence of the event;
- a first sensor for determining first real-time parameter values;
- a second sensor for determining second real-time parameter values;
- an analysis component for analyzing the first real-time parameter values relative to the first reference parameter values, and responsive to determining a first predetermined relationship therebetween, then activating the second sensor and analyzing the second real-time parameter values relative to the second reference parameter values; and
- responsive to results of analysis of the first and second real-time parameter values, a communications component for issuing a notification that an event has occurred.

25. The system of claim 24, wherein the first sensor comprises a first plurality of sensors and the second sensor comprise a second plurality of sensors, and one or more of the first plurality of sensors are included within the second plurality of sensors.

26. The system of claim 25, wherein there is at least one real-time parameter value determined by the second plurality of sensors that was not determined by the first plurality of sensors.

27. The system of claim 24, wherein the first sensor is activated based on time, time intervals, activities of a monitored person, the monitored person entering or leaving a location or area, or manually.

28. The system of claim 24, wherein the first and second real-time parameters are measured concurrently.

29. The system of claim 24, further comprising a location determining component for determining when a monitored person is in a safe zone, notifications not issued when the monitored person is in the safe zone.

30. A wearable device embodying the system of claim 24, wherein the event comprises that a person wearing the wearable has fallen and the first and second real-time parameter values are derived from an accelerometer, a gyroscope, an altimeter, or a pressure detector.

* * * * *